United States Patent [19]

Inaba et al.

[11] Patent Number: 4,540,800

[45] Date of Patent: Sep. 10, 1985

[54] PREPARATION OF 2,3-DIHYDRO-2-METHYL-2,3-DIALKYL-7-OXYBENZOFURANS

[75] Inventors: Yukio Inaba; Taisei Igarashi; Susumu Tahara; Takashi Miyatake, all of Ube, Japan

[73] Assignee: Ube Industries, Ltd., Ube, Japan

[21] Appl. No.: 484,237

[22] Filed: Apr. 12, 1983

[30] Foreign Application Priority Data

Apr. 22, 1982 [JP] Japan .................................. 57-66286
Apr. 22, 1982 [JP] Japan .................................. 57-66287

[51] Int. Cl.³ .......................................... C07D 307/86
[52] U.S. Cl. ..................................... 549/462; 549/437
[58] Field of Search ......................................... 549/462

[56] References Cited

U.S. PATENT DOCUMENTS 3,598,842  8/1971  Martini ................................ 549/458
4,118,400 10/1978  Michaely ............................. 549/462

Primary Examiner—Henry R. Jiles
Assistant Examiner—Bernard I. Dentz
Attorney, Agent, or Firm—Frishauf, Holtz, Goodman & Woodward

[57] ABSTRACT

A process for the preparation of a 2,3-dihydro-2-methyl-2,3-dialkyl-7-oxybenzofuran having the formula (I):

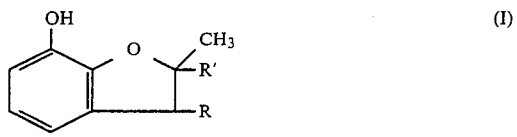

in which R and R' are the same or different and each represents a lower alkyl group or hydrogen atom, which comprises reacting catechol with an aldehyde having the formula (II):

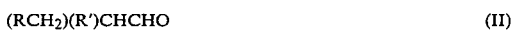

or an alcohol having the formula (III):

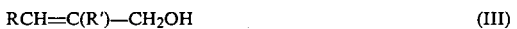

in a gaseous phase in the presence of a solid acid catalyst. The products are useful as intermediates in the preparation of insecticides.

18 Claims, No Drawings

PREPARATION OF 2,3-DIHYDRO-2-METHYL-2,3-DIALKYL-7-OXYBENZOFURANS

This invention relates to a process for the preparation of a 2,3-dihydro-2-methyl-2,3-dialkyl-7-oxybenzofuran that is of value as an intermediate compound for the preparation of carbofuran. The carbofuran is of value as insecticide.

A variety of processes for the preparation of a 2,3-dihydro-2-methyl-2,3-dialkyl-7-oxybenzofuran have been proposed until now.

For instance, Japanese Patent Provisional Publication No. 56(1981)-29584 describes a process comprising reacting catechol with 2-methylallyl chloride in a liquid phase (in a polyhydroxyalkyl ether solvent) in the presence of a base to give catechol mono(2-methylallyl)ether and then cyclizing the so obtained ether under heating.

Japanese Patent Provisional Publication No. 54(1979)-48752 describes a process comprising reacting catechol with isobutylaldehyde in a liquid phase (in benzene) in the presence of sulfuric acid to give 2-isopropyl-1,3-benzodioxol and then heating the so obtained benzodioxol.

The former proces requires a solvent for carrying out the liquid phase reaction, and further requires a corrosion-resistant reaction vessel because corrosive chloride and alkali are employed. Further, this process produces a great amount of a by-product, namely, sodium chloride.

The latter process likewise requires a solvent for carrying out the liquid phase reaction. Further, this process is disadvantageous in that the yield of the first stage reaction is extremely low and the conversion ratio of the second stage is also low.

The present invention provides a process for preparing the above-mentioned oxybenzofuran derivatives in a single stage and in satisfactory yields.

There is provided by the invention a process for the preparation of a 2,3-dihydro-2-methyl-2,3-dialkyl-7-oxybenzofuran having the formula (I):

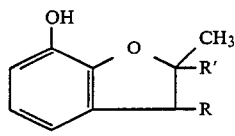
(I)

in which R and R' are the same or different and each represents a lower alkyl group or hydrogen atom, which comprises reacting catechol with an aldehyde having the formula(II):

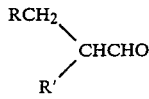
(II)

in which R and R' are as defined above, or an alcohol having the formula (III):

RCH=C—CH₂OH
      |
      R'   (III)

in which R and R' are as defined above, in a gaseous phase in the presence of a solid acid catalyst.

In the above description, the lower alkyl group preferably is an alkyl group having 1–6 carbon atoms.

Examples of the aldehyde having the formula (II) include isobutylaldehyde, butylaldehyde, propionaldehyde, 2-methylbutylaldehyde, 2-ethylbutylaldehyde, and amylaldehyde.

Examples of the alcohol having the formula (III) include 2-methylallyl alcohol, allyl alcohol and 2-ethylallyl alcohol.

In carrying out the reaction, the catechol and the aldehyde or alcohol are preferably employed in the ratio of 1:1 to 1:5 (ratio by weight).

The reaction can be carried out by vaporizing separately each of catechol and the aldehyde or alcohol. Otherwise, a mixture of catechol and the aldehyde or alcohol can be vaporized for the reaction.

Examples of the solid acid catalyst to be employed in the process of the invention include silica, alumina, magnesia, boria, silica-alumina, silica-magnesia, alumina-boria, phosphoric acid-alumina, phosphoric acid-boria, acid clay and diatomaceous earth. The solid acid catalyst can be employed as such, but the solid acid catalyst preferably carries a noble metal such as palladium or platinum in the amount of 0.1 to 1 percent by weight of the catalyst.

The solid acid catalyst deteriorated upon the reaction can be regenerated through burning the attached carbon by bringing the catalyst in contact with a stream of air, oxygen or the like at an elevated temperature.

There is no limination of shape of the solid acid catalyst, and as the shape there can be mentioned granules, haneycomb, and pellets.

The reaction of the process according to the invention can be generally carried out at a temperature in the range of 200° to 300° C., preferably in the range of 220° to 260° C. The reaction is generally carried out at an atmospheric pressure, but a slightly enhanced or reduced pressure can be also utilized.

The reaction is generally carried out over a fixed bed, but a moving bed or a fluidized bed can be also employed.

The product obtained by the reaction in a gaseous phase in the presence of a solid acid catalyst comprises the desired 2,3-dihydro-2-methyl-2,3-dialkyl-7-oxybenzofuran having the aforementioned formula (I) and by-products such as 2-(1', 2'-dialkylethyl)-1,3-benzodioxol.

Examples of the desired oxybenzofuran derivative of the invention include 2,3-dihydro-2,2-dimethyl-7-oxybenzofuran and 2,3-dihydro-2,2,3-trimethyl-7-oxybenzofuran.

The desired benzofuran derivative of the formula (I) can be isolated through a conventional procedure such as distillation or extraction.

The above-mentioned by-product, 2-(1',2'-dialkylethyl)-1,3-benzodioxol has the formula (IV):

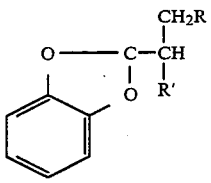
(IV)

(R an R' are as defined as hereinbefore), and can be employed as a starting compound for the preparation of the desired 2,3-dihydro-2-methyl-2,3-dialkyl-7-oxybenzofuran having the aforementioned formula (I).

Examples of the above-mentioned benzodioxol derivative having the formula (IV) include 2-isopropyl-1,3-benzodioxol, 2-(1'-methylpropyl)-1,3-benzodioxol, and 2-propyl-1,3-benzodioxol.

The reaction of the 2-(1',2'-dialkylethyl)-1,3-benzodioxol for the preparation of the desired 2,3-dihydro-2-methyl-2,3-dialkyl-7-oxybenzofuran can be carried out in a gaseous phase in the presence of a solid acid catalyst.

The reaction conditions and solid acid catalyst of the above-mentioned reaction can be selected from those described hereinbefore in respect to the reaction between catechol and the aldehyde having the formula (II) or the alcohol having the formula (III).

The present invention is further described by the following examples, which are understood by no means to restrict the invention.

In Examples 1–13, the reaction ratio (%), selection ratio (%) and yield (%) are defined as follows:

$$\text{Reaction Ratio (\%)} = \frac{\text{Moles of Reacted Catechol}}{\text{Moles of supplied Catechol}} \times 100$$

$$\text{Selection Ratio (\%)} = \frac{\text{Moles of Produced Benzofuranol}}{\text{Moles of Reacted Catechol}} \times 100$$

$$\text{Yield (\%)} = \frac{\text{Moles of Produced Benzofuranol}}{\text{Moles of Supplied Catechol}} \times 100$$

In the above equations, benzofuranol means 2,3-dihydro-2-methyl-2,3-dialkyl-7-oxybenzofuran.

In Examples 14–16, the reaction ratio (%), selection ratio (%) and yield (%) are defined as follows:

$$\text{Reaction Ratio (\%)} = \frac{\text{Moles of Reacted Benzoxol}}{\text{Moles of Supplied Benzoxol}} \times 100$$

$$\text{Selection Ratio (\%)} = \frac{\text{Moles of Produced Benzofuranol}}{\text{Moles of Reacted Benzoxol}} \times 100$$

$$\text{Yield (\%)} = \frac{\text{Moles of Produced Benzofuranol}}{\text{Moles of Supplied Benzoxol}} \times 100$$

In the above equations, benzoxol means 2-(1',2'-dialkylethyl)-1,3-benzoxol, and benzofuranol is as defined above.

EXAMPLE 1

In a vaporizer filled with Raschig rings, catechol and isobutylaldehyde were heated to 220° C. to produce a vapor mixture of catechol and isobutylaldehyde (1:4, ratio by weight). The vapor mixture was passed through a catalyst layer of a hollow molded product (inner diameter 40 mm × height 1,000 mm) deposited with 0.2% Pt-Al$_2$O$_3$ at 260° C. at the rate of 300 cc./hr. to carry out continuous reaction.

Thus, 2,3-dihydro-2,2-dimethyl-7-oxybenzofuran was obtained: reaction ratio 30%, selection ratio 72%, and yield 21.6%.

EXAMPLE 2

The procedures of Example 1 were repeated except that the 0.2% Pt-Al$_2$O$_3$ was replaced with γalumina.

There was obtained 2,3-dihydro-2,2-dimethyl-7-oxybenzofuran: reaction ratio 20%, selection ratio 65%, and yield 13%.

EXAMPLE 3

The procedures of Example 1 were repeated except that the combination of catechol and isobutylaldehyde were replaced with a combination of catechol and 2-methylallyl alcohol in the ratio of 1:4 by weight.

There was obtained 2,3-dihydro-2,3-dimethyl-7-oxybenzofuran: reaction ratio 40%, selection ratio 85%, and yield 34%.

EXAMPLE 4

The procedures of Example 1 were repeated except that the 0.2% Pt-Al$_2$O$_3$ and the combination of catechol and isobutylaldehyde were replaced with 0.2% Pt-P$_2$O$_5$-Al$_2$O$_3$ and a combination of catechol and 2-methylbutylaldehyde in the ratio of 1:4 by weight.

There was obtained 2,3-dihydro-2,2,3-trimethyl-7-oxybenzofuran: reaction ratio 30%, selection ratio 68%, and yield 19.5%.

EXAMPLES 5–13

The procedures of Example 1 were repeated except that the 0.2% Pt-Al$_2$O$_3$ and the reaction temperature were replaced with the solid acid catalyst and the temperature set forth in Table 1.

There was obtained 2,3-dihydro-2,2-dimethyl-7-oxybenzofuran. The reaction ratio, selection ratio and yield are set forth in Table 1.

TABLE 1

| Example | Catalyst | Temp. (°C.) | Reaction Ratio (%) | Selection Ratio (%) | Yield (%) |
|---|---|---|---|---|---|
| 5 | Silica - Alumina | 260 | 25 | 50 | 12.5 |
| 6 | Silica - Magnesia | 280 | 30 | 55 | 16.5 |
| 7 | Magnesia | 280 | 35 | 65 | 22.8 |
| 8 | Silica | 300 | 25 | 50 | 12.5 |
| 9 | Diatomaceous earth | 300 | 20 | 50 | 10.0 |
| 10 | Acid Clay | 300 | 20 | 45 | 9.0 |
| 11 | P$_2$O$_5$—Alumina | 260 | 30 | 55 | 16.5 |
| 12 | P$_2$O$_5$—Boria | 260 | 20 | 45 | 9.0 |
| 13 | Alumina - Boria | 280 | 15 | 45 | 6.8 |

EXAMPLE 14

In a vaporizer filled with Raschig rings, 2-isopropyl-1,3-benzodioxol was heated to 250° C. to vaporize, and the vapor was subsequently passed through a catalyst layer of a hollow molded product (inner diameter 40 mm × height 1,000 mm) deposited with 0.2% Pt-Al$_2$O$_3$ at 300° C. at the rate of 100 cc./hr. to carry out continuous reaction.

Thus, 2,3-dihydro-2,2-dimethyl-7-oxybenzofuran was obtained: reaction ratio 30%, selection ratio 55%, and yield 16.5%.

EXAMPLE 15

The procedures of Example 14 were repeated except that the 0.2% Pt-Al$_2$O$_3$ was replaced with SiO$_2$-Al$_2$O$_3$.

There was obtained 2,3-dihydro-2,2-dimethyl-7-oxybenzofuran: reaction ratio 40%, selection ratio 40%, and yield 16%.

EXAMPLE 16

The procedures of Example 14 were repeated except that the 0.2% Pt-Al$_2$O$_3$ was replaced with P$_2$O$_5$-Al$_2$O$_3$.

There was obtained 2,3-dihydro-2,2-dimethyl-7-oxybenzofuran: reaction ratio 20%, selection ratio 45%, and yield 9%.

We claim:

1. A process for the preparation of a 2,3-dihydro-2-methyl-2,3-dialkyl-7-oxybenzofuran having the formula (I):

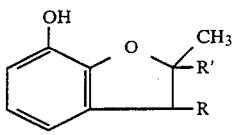

wherein R and R' are the same or different and each represents a lower alkyl group or hydrogen atom, which comprises reacting catechol with an aldehyde having the formula (II)

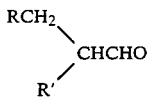

or an alcohol having the formula (III):

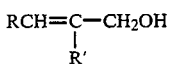

in a gaseous phase in the presence of a solid acid catalyst.

2. The process as claimed in claim 1, wherein the aldehyde or alcohol is selected from the group consisting of isobutylaldehyde, butylaldehyde, propionaldehyde, 2-methylbutylaldehyde, 2-ethylbutylaldehyde, amylaldehyde, 2-methylallyl alcohol, allyl alcohol, and 2-ethylallyl alcohol.

3. The process as claimed in claim 1, wherein catechol and the aldehyde or alcohol is employed in a ratio by weight of 1:1–1:5.

4. The process as claimed in claim 1, wherein the solid acid catalyst is selected from the group consisting of silica, alumina, magnesia, boria, silica-alumina, silica-magnesia, alumina-boria, phosphoric acid-alumina, phosphoric acid-boria, acid clay and diatomaceous earth.

5. The process as claimed in claim 4, wherein the solid acid catalyst carries a noble metal in the amount of 0.1 to 1 percent by weight.

6. The process as claimed in claim 1, wherein the reaction is carried out at a temperature of 200°–300° C.

7. The process as claimed in claim 6, wherein the aldehyde or alcohol is selected from the group consisting of isobutylaldehyde, butylaldehyde, propionaldehyde, 2-methylbutylaldehyde, 2-ethylbutylaldehyde, amylaldehyde, 2-methylallyl alcohol, allyl alcohol, and 2-ethylallyl alcohol.

8. The process as claimed in claim 7, wherein catechol and the aldehyde or alcohol is employed in a ratio by weight of 1:1–1:5.

9. The process as claimed in claim 8, wherein the solid acid catalyst is selected from the group consisting of silica, alumina, magnesia, boria, silica-alumina, silica-magnesia, alumina-boria, phosphoric acid-alumina, phosphoric acid-boria, acid clay and diatomaceous earth.

10. The process as claimed in claim 9, wherein the solid acid catalyst carries a noble metal in the amount of 0.1 to 1 percent by weight.

11. The process as claimed in claim 2, wherein catechol and the aldehyde or alcohol is employed in a ratio by weight of 1:1–1:5, and wherein the solid acid catalyst is selected from the group consisting of silica, alumina, magnesia, boria, silica-alumina, silica-magnesia, alumina-boria, phosphoric acid-alumina, phosphoric acid-boria, acid clay and diatomaceous earth.

12. The process as claimed in claim 11, wherein the solid acid catalyst carries a noble metal in the amount of 0.1 to 1 percent by weight.

13. The process as claimed in claim 3, wherein the solid acid catalyst is selected from the group consisting of silica, alumina, magnesia, boria, silica-alumina, silica-magnesia, alumina-boria, phosphoric acid-alumina, phosphoric acid-boria, acid clay and diatomaceous earth.

14. The process as claimed in claim 13, wherein the aldehyde or alcohol is selected from the group consisting of isobutylaldehyde, butylaldehyde, propionaldehyde, 2-methylbutylaldehyde, 2-ethylbutylaldehyde, amylaldehyde, 2-methylallyl alcohol, allyl alcohol, and 2-ethylallyl alcohol, and wherein the solid acid catalyst carries a noble metal in the amount of 0.1 to 1 percent by weight.

15. The process as claimed in claim 10, wherein the catechol is reacted with an aldehyde.

16. The process as claimed in claim 10, wherein the catechol is reacted with an alcohol.

17. The process as claimed in claim 1, wherein the catechol is reacted with an aldehyde.

18. The process as claimed in claim 1, wherein the catechol is reacted with an alcohol.

* * * * *